United States Patent [19]

Junginger

[11] Patent Number: 5,837,114
[45] Date of Patent: Nov. 17, 1998

[54] ARRANGEMENT FOR DETERMINING THE CONCENTRATION OF A COMPONENT IN A GAS MIXTURE

[75] Inventor: Erich Junginger, Stuttgart, Germany

[73] Assignee: Robert Bosch GmbH, Stuttgart, Germany

[21] Appl. No.: 765,735

[22] PCT Filed: Mar. 29, 1996

[86] PCT No.: PCT/DE96/00611

§ 371 Date: Jan. 13, 1997

§ 102(e) Date: Jan. 13, 1997

[87] PCT Pub. No.: WO96/35120

PCT Pub. Date: Nov. 7, 1996

[30] Foreign Application Priority Data

May 3, 1995 [DE] Germany .................. 195 16 139.4

[51] Int. Cl.[6] .................................................. G01N 27/26
[52] U.S. Cl. ...................... 204/425; 204/427; 123/672; 123/693; 123/694; 123/703
[58] Field of Search ................................. 204/425, 427; 123/672, 693, 694, 703

[56] References Cited

U.S. PATENT DOCUMENTS

| | | | |
|---|---|---|---|
| 4,622,126 | 11/1986 | Shimomura | 204/425 |
| 4,658,790 | 4/1987 | Kitahara | 123/440 |
| 4,772,376 | 9/1988 | Yukawa et al. | 204/410 |
| 5,236,569 | 8/1993 | Murase et al. | 204/412 |
| 5,338,431 | 8/1994 | Yorita et al. | 204/424 |
| 5,366,610 | 11/1994 | Hirako et al. | 204/425 |
| 5,391,284 | 2/1995 | Hötzel | 204/425 |
| 5,549,804 | 8/1996 | Hötzel et al. | 204/425 |
| 5,558,752 | 9/1996 | Wang et al. | 204/425 |

OTHER PUBLICATIONS

"Universal Air–Fuel Ratio Heated Exhaust Gas Oxygen Sensor and Further Applications" by T. Yamada et al, SAE Technical Paper Series 920234, International Congress & Exposition, Detroit, MI, Feb. 24–28, 1992.

*Primary Examiner*—Bruce F. Bell
*Attorney, Agent, or Firm*—Walter Ottesen

[57] ABSTRACT

An arrangement for determining the concentration of a component in a gas mixture includes a first volume in which the concentration of the component is maintained constant with respect to the influence of the coupling to the concentration in the gas mixture. The coupling acts via a diffusion resistance. The above-mentioned influence of the coupling is compensated via a controllable flow of ions of the component through a solid electrolyte between the first volume and the gas mixture. The solid electrolyte serves as the pump device. The intensity of the pump current defines a measure for the wanted concentration in the gas mixture. The above-mentioned flow is controlled as a function of the deviation of the output voltage of a Nernst cell from a desired value. The Nernst cell is between a first volume and a reference gas volume. The arrangement is characterized by means which influence the above-mentioned desired value in dependence upon the voltage which can be measured across the solid electrolyte of the pump device.

5 Claims, 3 Drawing Sheets

ARRANGEMENT FOR DETERMINING THE CONCENTRATION OF A COMPONENT IN A GAS MIXTURE

This application is a 371 of PCT/DE96/00611 filed Mar. 29, 1996.

FIELD OF THE INVENTION

The invention relates to an arrangement for determining the concentration of a component in a gas mixture. The invention is especially related to measurement sensors which are utilized for controlling the composition of the air/fuel mixture of internal combustion engines. Sensors of this kind detect the oxygen content in the exhaust gas of the engine and supply an input signal for a control loop to control the mixture composition to pregiven values.

BACKGROUND OF THE INVENTION

The subject matter of the invention is an arrangement which is configured, in principle, as a universal oxygen probe described in SAE Paper 920234.

A probe of the type disclosed therein has a first component volume in which the concentration of oxygen is coupled via a diffusion resistance to the concentration of oxygen in the exhaust gas. An atmosphere having a reference oxygen concentration is present in a second component volume. A Nernst cell is mounted between the first and second component volumes and supplies an output signal characteristic of the difference of the oxygen concentrations in the two component volumes. A deviation of the oxygen concentration in the first volume, which is coupled to the exhaust gas, from a desired value is determined by comparing this output signal to a pregiven value. An oxygen pump device pumps oxygen particles into the first component volume or pumps oxygen particles out of this first component volume at a flow intensity which is dependent upon the determined deviation so that the oxygen concentration can there be held constant against the influence of the coupling to the oxygen concentration in the exhaust gas with the coupling acting via the diffusion resistance.

The variable which is to be determined, namely the oxygen concentration in the exhaust gas, can be determined by evaluating the pump current Ip.

An advantage of oxygen probes of this type is the approximately linear characteristic line Ip=f(lambda) which results when there is a slow continuous change of the mixture composition lambda. If the mixture composition is however modulated more rapidly as is conventional for the mixture control for engines, a hysteresis in the characteristic line results at lambda=1. Stated otherwise, the value of the output signal of the sensor in the vicinity of lambda=1 is dependent upon the direction of the change of the mixture composition.

SUMMARY OF THE INVENTION

The object of the present invention is to eliminate these hysteresis effects and provide a sensor of the above-mentioned type having a characteristic line which does not exhibit disturbing hysteresis effects.

This object is solved by providing an arrangement for determining the concentration of a component in a gas mixture, the arrangement having a first volume in which the concentration of the component is held constant with respect to the influence of the coupling to the concentration in the gas mixture, the coupling acting via a diffusion resistance; the above-mentioned influence of the coupling is compensated by a controllable flow of ions of the component through a solid electrolyte between the first volume and the gas mixture so that a measure for the above-mentioned flow defines a measure for the wanted concentration in the gas mixture, the solid electrolyte functioning as a pump device; the above-mentioned flow is controlled as a function of the deviation of the output voltage of a Nernst cell and a desired value, the Nernst cell being between the first volume and a reference gas volume; and, means are provided which influence the above-mentioned desired value in a targeted manner as a function of the voltage which can be measured across the solid electrolyte of the pump device.

The use of the arrangement of the invention especially increases the accuracy of control loops having a continuous dependency of the position variable from the control deviation in the range which is essential for the conversion of toxic materials when there is a stoichiometric mixture composition (lambda=1).

BRIEF DESCRIPTION OF THE DRAWINGS

In the following, the invention is explained in greater detail with respect to an example and with respect to the enclosed drawings.

DESCRIPTION OF THE PREFERRED EMBODIMENTS OF THE INVENTION

Figure 1:
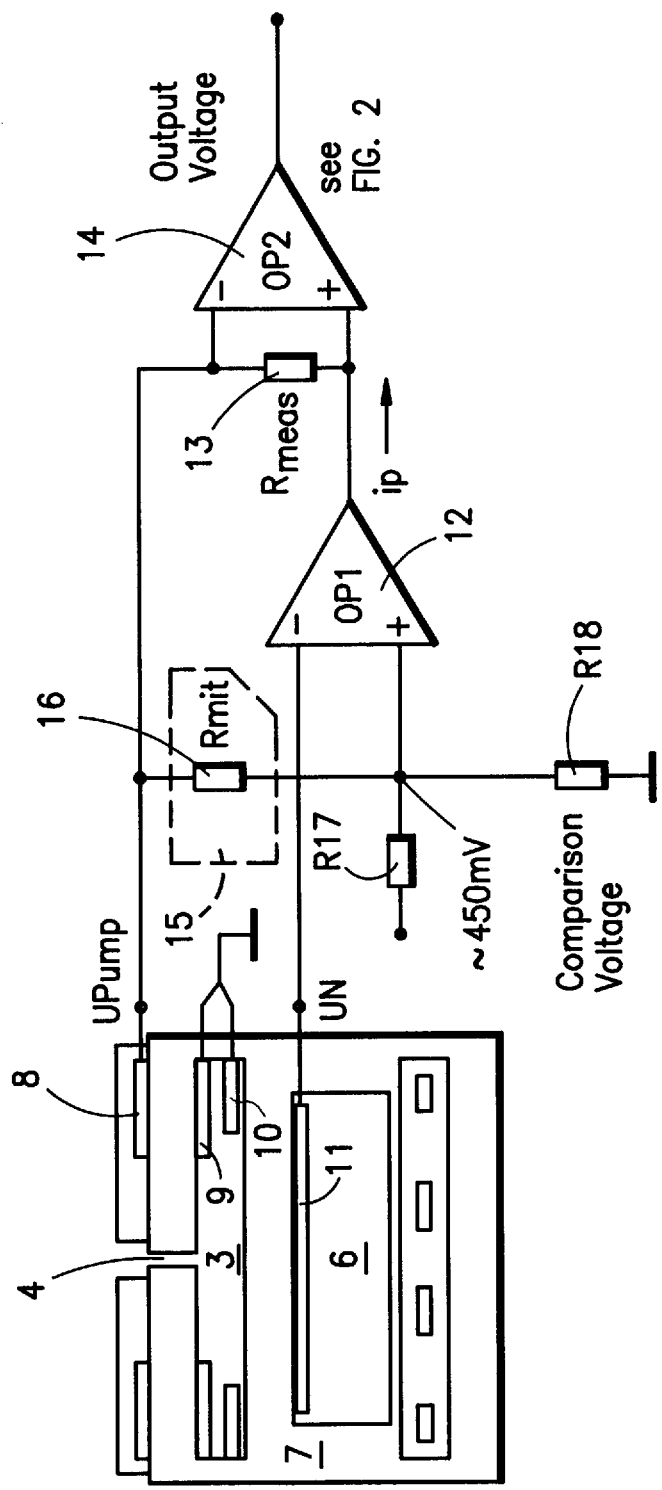
FIG. 1 is an embodiment of the arrangement of the invention.

The arrangement shown in FIG. 1 comprises a sensor 1 and the circuitry 2 of the sensor. The actual sensor 1 includes a first component volume 3 which is connected to the exhaust gas 5 via a diffusion resistance 4 realized here as a small opening. A reference atmosphere is present in a second component volume 6. This reference atmosphere can be defined by a connection to the external air or can be generated in some other way. Both component volumes are delimited by an oxygen-ion conducting electrolyte 7 which supports electrodes 8, 9, 10 and 11.

The Nernst voltage UN adjusts as a consequence of the different oxygen concentrations in the two component volumes 3 and 6. The Nernst voltage UN is supplied to the inverting input of a first operational amplifier 12 and a pregiven comparison voltage of, for example, 450 millivolt is applied to the non-inverting input. A desired value for the oxygen concentration in the first component volume is determined with the comparison voltage. If the Nernst voltage UN is less than 450 millivolts, then the output of the operational amplifier 12 is positive and drives a positive current through the pump cell defined by the electrodes (8, 9) and the electrolyte disposed therebetween. Stated otherwise, a comparatively low Nernst voltage leads to a transport of (negative) oxygen ions from the first component volume to the exhaust gas. The comparatively small Nernst voltage corresponds to an excess of oxygen in the first component volume. In a like manner, a comparatively high Nernst voltage leads to an oxygen particle current from the exhaust gas to the first component volume so that, in the steady-state condition, a pregiven concentration of oxygen adjusts in the first component volume. Since this concentration is disturbed by the coupling acting via the diffusion resistance 4, the pump current Ip defines a criterion for the concentration of the oxygen in the exhaust gas. The pump current Ip is necessary for maintaining.

The pump current Ip can, as shown in FIG. 1, be measured as a voltage drop across a measuring resistor 13 via a second operational amplifier 14.

Figure 2:
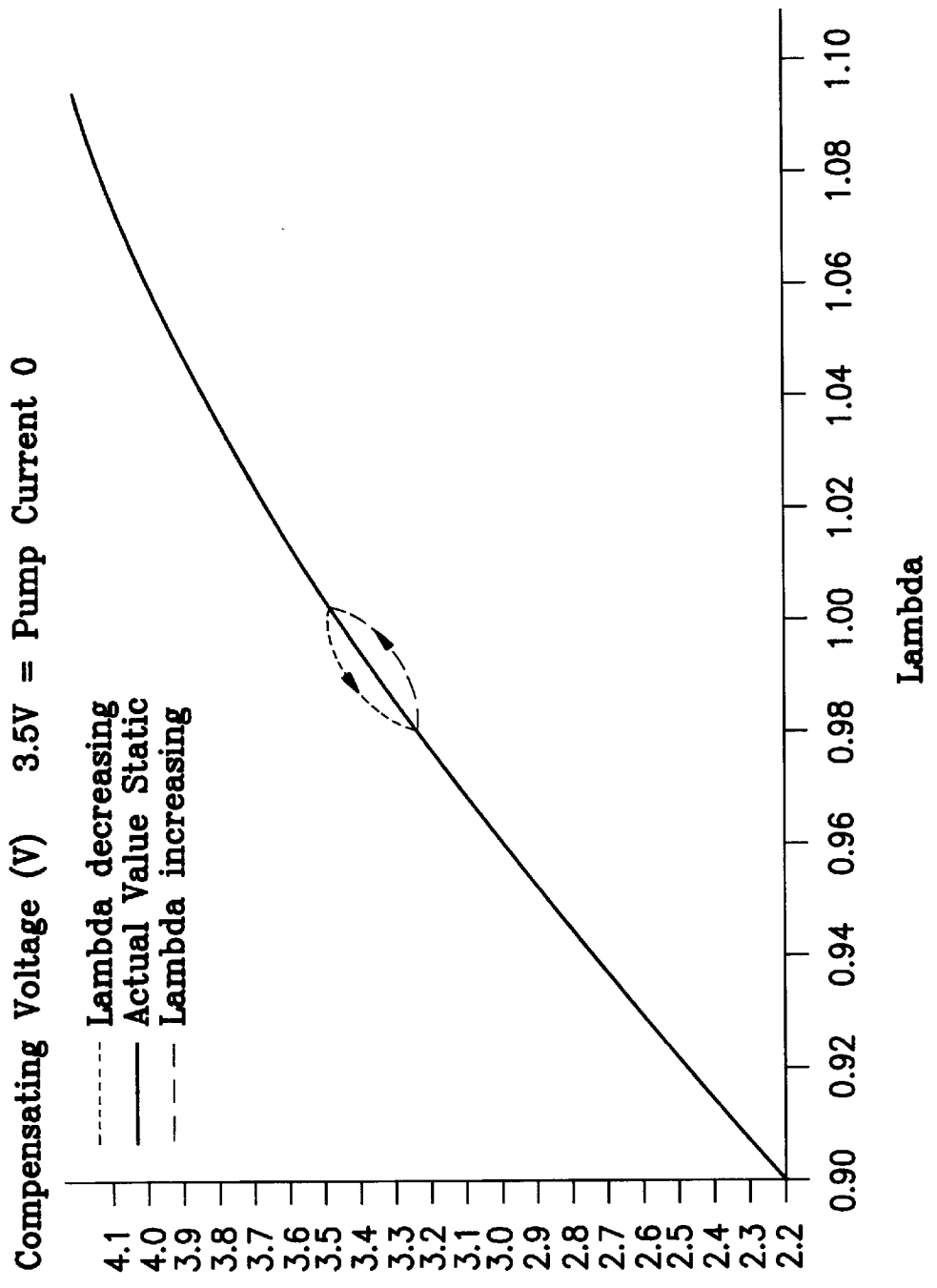
FIG. 2 shows a comparison of the traces of the characteristic lines of the output signal of the oxygen measuring devices of the state of the art and of the invention.
Figure 3:
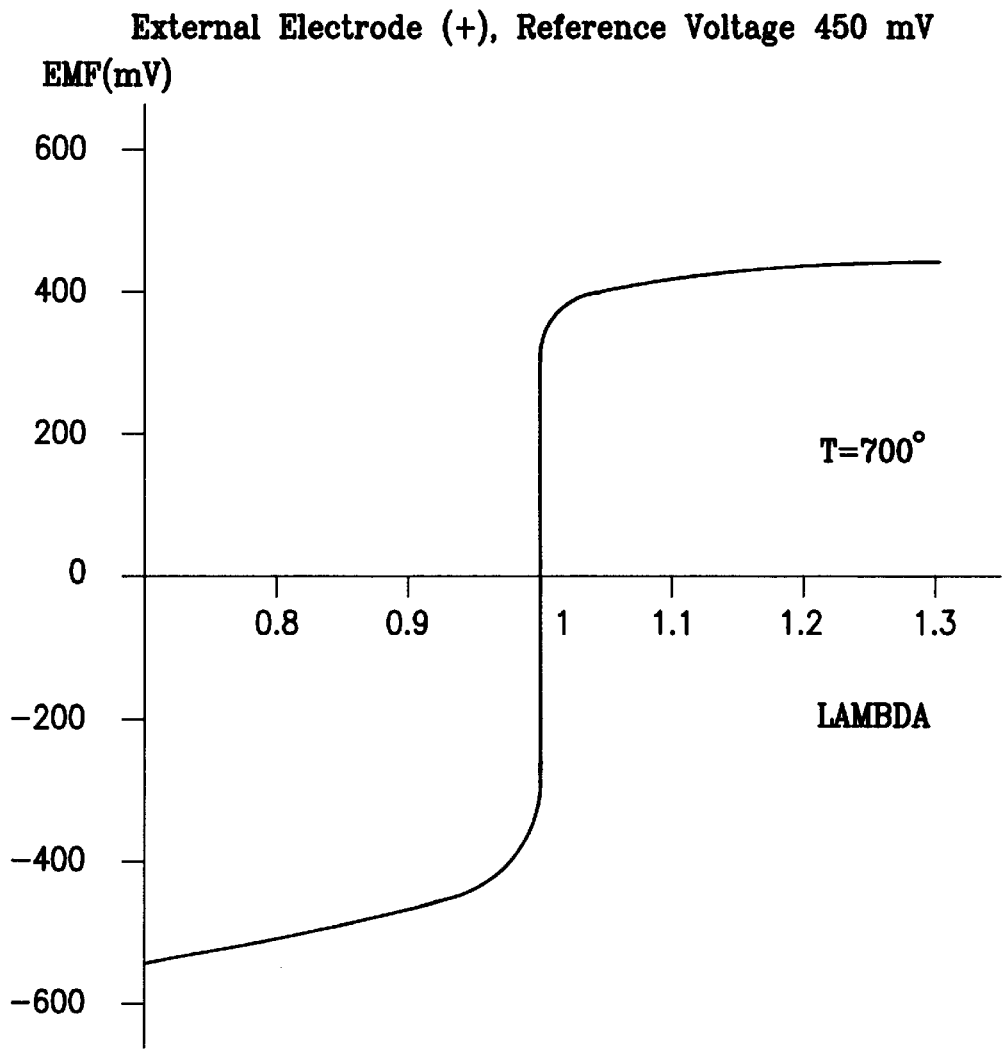
FIG. 3 shows the voltage, which can be measured across the electrolyte of the pump device, for an arrangement of FIG. 1 having a reference voltage of 450 millivolts across the mixture composition fluctuating from lambda=0.7 to 1.3.

The arrangement described above corresponds to the state of the art. The arrangement supplies an output signal as shown by the broken lines in the characteristic lines of FIG. 2. The unwanted hysteresis effects at lambda=1 are dependent upon the jump-like change of the EMF of the pump cell at lambda=1 (see FIG. 3). A disturbing coupling of the jump-like change to the Nernst voltage UN results because of the coupling (given by the structure) of the pump cell to the Nernst cell.

The change of the Nernst voltage UN is controlled out via the pump current which causes an unwanted change of the output signal of the sensor measured via the measuring resistor 13. The hysteresis effects in the output signal then show lambda changes which are not present. In order to prevent this, and according to the invention, a part of the EMF of the pump cell is directly fed back via a means 15 to the comparison voltage.

The means 15 can, for example, be realized by an ohmic resistance Rmit 16. The value of Rmit is advantageously so selected that the comparison voltage changes to the same extent as the Nernst voltage UN for changes of the EMF of the pump cell. No disturbing pump current change then occurs when there is a passthrough through lambda=1 of the oxygen concentration in the exhaust gas. Accordingly, the output voltage of the sensor according to the invention is then clear at this position.

In the embodiment shown, the comparison voltage is essentially determined by the measuring resistors R17 and R18. If the direct feedback M is defined as:

$$M = \frac{\frac{R17*R18}{R17+R18}}{Rmit + \frac{R17*R18}{R17+R18}}$$

then the comparison voltage changes by 10 millivolts for a direct feedback M=0.02 and values for Rmit=980 kiloohm and R17/R18=20 kiloohm when the pump cell EMF changes by 500 millivolts.

Figure 4A:
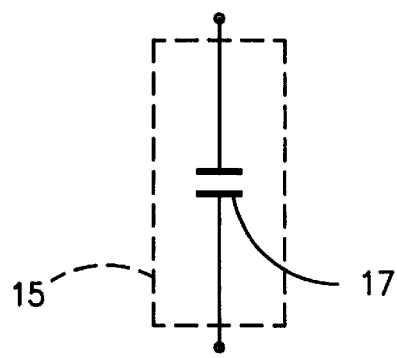
FIG. 4a and 4b show alternatives for influencing the desired value in accordance with the invention.
Figure 4B:
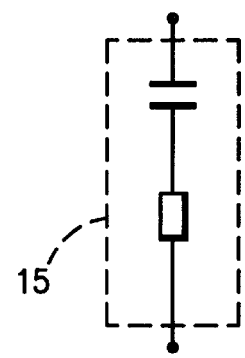

FIG. 4 illustrates alternative realizations for providing proportional direct feedback utilizing an ohmic resistor 16. These realizations result from an integral direct feedback via a capacitor 17 in lieu of Rmit (FIG. 4a) or via a series circuit of a capacitor and an ohmic resistor in lieu of Rmit (FIG. 4b).

The use of the sensor according to the invention is not limited to the measurement of the concentration of oxygen. The invention can also be applied to measure other concentrations by utilizing electrolytes which are conductive for ions of other gas components.

I claim:

1. An arrangement for determining the concentration of a component in a gas mixture, the arrangement comprising:

a structure defining a first volume;

diffusion resistance means defining a coupling between said first volume and said gas mixture;

said first volume holding the concentration of said component constant in opposition to the influence of said coupling;

said structure including a solid electrolyte region between said gas mixture and said first volume;

pump circuit means connected to said solid electrolyte region for controlling a flow of ions of said component through said first electrolyte region to compensate for said influence so that a measure for said flow defines a measure for the wanted concentration of said component in said gas mixture;

said structure including a second volume for accommodating a reference concentration of said component therein;

supply means for supplying a comparison voltage;

a Nernst cell arranged between said first and second volumes for supplying a Nernst voltage dependent upon the respective concentrations of said component in said first and second volumes;

ancillary circuit means connected to said supply means and said Nernst cell for supplying an output current to said pump circuit means indicative of the difference between said comparison voltage and said Nernst voltage thereby controlling said flow of said ions of said component of said gas mixture and producing a drive voltage across said solid electrolyte region which can be measured; and, feedback means for influencing said comparison voltage as a function of said drive voltage.

2. The arrangement of claim 1, said feedback means including an ohmic resistor means (Rmit) for feeding a portion of said drive voltage to said comparison voltage.

3. The arrangement of claim 1, said feedback means including a capacitor for feeding a portion of said drive voltage to said comparison voltage.

4. The arrangement of claim 1, said feedback means including a series circuit for feeding a portion of said drive voltage to said comparison voltage; and, said series circuit including an ohmic resistor and a capacitor.

5. The arrangement of claim 1, said coupling being so dimensioned that said comparison voltage changes to the same extent as said Nernst voltage when there is a change of said drive voltage.

* * * * *